US 8,142,486 B2
Mar. 27, 2012

(12) United States Patent
Quisenberry et al.

(10) Patent No.: US 8,142,486 B2
(45) Date of Patent: Mar. 27, 2012

(54) WOUND CARE METHOD AND SYSTEM WITH ONE OR BOTH OF VACUUM-LIGHT THERAPY AND THERMALLY AUGMENTED OXYGENATION

(75) Inventors: Tony Quisenberry, Highland Village, TX (US); Niran Balachandran, Lewisville, TX (US)

(73) Assignee: ThermoTek, Inc., Flower Mound, TX (US)

( * ) Notice: Subject to any disclaimer, the term of this patent is extended or adjusted under 35 U.S.C. 154(b) by 0 days.

(21) Appl. No.: 13/190,564

(22) Filed: Jul. 26, 2011

(65) Prior Publication Data

US 2011/0282269 A1 Nov. 17, 2011

Related U.S. Application Data

(63) Continuation of application No. 11/975,047, filed on Oct. 17, 2007, which is a continuation-in-part of application No. 11/801,662, filed on May 9, 2007.

(60) Provisional application No. 60/852,803, filed on Oct. 19, 2006, provisional application No. 60/798,982, filed on May 9, 2006.

(51) Int. Cl.
*A61N 5/06* (2006.01)

(52) U.S. Cl. .......................... 607/88; 128/898

(58) Field of Classification Search ............... 607/88–90; 128/898
See application file for complete search history.

(56) References Cited

U.S. PATENT DOCUMENTS

| 773,828 A | 11/1904 | Titus et al. |
|---|---|---|
| 2,110,022 A | 3/1938 | Kliesrath |
| 2,504,308 A | 4/1950 | Donkle, Jr. |
| 3,014,117 A | 12/1961 | Madding |
| 3,164,152 A | 1/1965 | Vere Nicoll |
| 3,345,641 A | 10/1967 | Jennings |
| 3,367,319 A | 2/1968 | Carter, Jr. |
| 3,608,091 A | 9/1971 | Olson et al. |
| 3,660,849 A | 5/1972 | Jonnes et al. |
| 3,736,764 A | 6/1973 | Chambers et al. |
| 3,738,702 A | 6/1973 | Jacobs |
| 3,744,053 A | 7/1973 | Parker et al. |
| 3,744,555 A | 7/1973 | Fletcher et al. |
| 3,862,629 A | 1/1975 | Rotta |
| 3,894,213 A | 7/1975 | Agarwala |
| 4,006,604 A | 2/1977 | Seff |
| 4,013,069 A | 3/1977 | Hasty |

(Continued)

FOREIGN PATENT DOCUMENTS

CH 670 541 6/1989

(Continued)

OTHER PUBLICATIONS

U.S. Appl. No. 29/402,115, Quisenberry.

(Continued)

*Primary Examiner* — Henry M Johnson, III
*Assistant Examiner* — Jeffrey Lipitz
(74) *Attorney, Agent, or Firm* — Winstead PC

(57) ABSTRACT

A system for treatment of a wound area of a patient including a first treatment pad comprising a plurality of Light Emitting Diodes (LEDs) for cleaning and exposing a wound area to ultraviolet light, a second treatment pad comprising removal ports for exposing the wound area to a negative pressure, and a control unit interoperably connected to the first and second treatment pads for providing a negative pressure and the ultraviolet light to the wound area.

15 Claims, 5 Drawing Sheets

U.S. PATENT DOCUMENTS

| | | |
|---|---|---|
| 4,206,751 A | 6/1980 | Schneider |
| 4,224,941 A | 9/1980 | Stivala |
| 4,375,217 A | 3/1983 | Arkans |
| 4,402,312 A | 9/1983 | Villari et al. |
| 4,459,468 A | 7/1984 | Bailey |
| 4,459,822 A | 7/1984 | Pasternack |
| 4,503,484 A | 3/1985 | Moxon |
| 4,547,906 A | 10/1985 | Nishida et al. |
| 4,597,384 A | 7/1986 | Whitney |
| 4,660,388 A | 4/1987 | Greene, Jr. |
| 4,741,338 A | 5/1988 | Miyamae |
| 4,821,354 A | 4/1989 | Little |
| 4,844,072 A | 7/1989 | French et al. |
| 4,884,304 A | 12/1989 | Elkins |
| 4,901,200 A | 2/1990 | Mazura |
| 4,911,231 A | 3/1990 | Horne et al. |
| 4,962,761 A | 10/1990 | Golden |
| 4,979,375 A | 12/1990 | Nathans et al. |
| 4,996,970 A | 3/1991 | Legare |
| 5,044,364 A | 9/1991 | Crowther |
| 5,051,562 A | 9/1991 | Bailey et al. |
| 5,067,040 A | 11/1991 | Fallik |
| 5,080,089 A | 1/1992 | Mason et al. |
| 5,090,409 A | 2/1992 | Genis |
| 5,092,271 A | 3/1992 | Kleinsasser |
| 5,097,829 A | 3/1992 | Quisenberry |
| 5,106,373 A | 4/1992 | Augustine et al. |
| 5,112,045 A | 5/1992 | Mason et al. |
| 5,125,238 A | 6/1992 | Ragan et al. |
| 5,165,127 A | 11/1992 | Nicholson |
| 5,179,941 A | 1/1993 | Siemssen et al. |
| 5,184,612 A | 2/1993 | Augustine |
| 5,186,698 A | 2/1993 | Mason et al. |
| 5,230,335 A | 7/1993 | Johnson, Jr. et al. |
| 5,232,020 A | 8/1993 | Mason et al. |
| 5,241,951 A | 9/1993 | Mason et al. |
| 5,243,706 A | 9/1993 | Frim et al. |
| 5,263,538 A | 11/1993 | Amidieu et al. |
| 5,285,347 A | 2/1994 | Fox et al. |
| D345,082 S | 3/1994 | Wenzl |
| D345,609 S | 3/1994 | Mason et al. |
| D345,802 S | 4/1994 | Mason et al. |
| D345,803 S | 4/1994 | Mason et al. |
| 5,300,101 A | 4/1994 | Augustine et al. |
| 5,300,102 A | 4/1994 | Augustine et al. |
| 5,300,103 A | 4/1994 | Stempel et al. |
| 5,303,716 A | 4/1994 | Mason et al. |
| 5,316,250 A | 5/1994 | Mason et al. |
| D348,106 S | 6/1994 | Mason et al. |
| 5,323,847 A | 6/1994 | Koizumi et al. |
| 5,324,319 A | 6/1994 | Mason et al. |
| 5,324,320 A | 6/1994 | Augustine et al. |
| D348,518 S | 7/1994 | Mason et al. |
| 5,330,519 A | 7/1994 | Mason et al. |
| 5,336,250 A | 8/1994 | Augustine |
| 5,343,579 A | 9/1994 | Dickerhoff et al. |
| 5,350,417 A | 9/1994 | Augustine |
| D351,472 S | 10/1994 | Mason et al. |
| 5,352,174 A | 10/1994 | Mason et al. |
| 5,354,117 A | 10/1994 | Danielson et al. |
| D352,781 S | 11/1994 | Mason et al. |
| 5,360,439 A | 11/1994 | Dickerhoff et al. |
| 5,370,178 A | 12/1994 | Agonafer et al. |
| 5,371,665 A | 12/1994 | Quisenberry et al. |
| D354,138 S | 1/1995 | Kelly |
| D357,747 S | 4/1995 | Kelly |
| 5,402,542 A | 4/1995 | Viard |
| 5,405,370 A | 4/1995 | Irani |
| 5,405,371 A | 4/1995 | Augustine et al. |
| 5,407,421 A | 4/1995 | Goldsmith |
| D358,216 S | 5/1995 | Dye |
| 5,411,494 A | 5/1995 | Rodriguez |
| 5,411,541 A | 5/1995 | Bell et al. |
| 5,417,720 A | 5/1995 | Mason |
| 5,440,450 A | 8/1995 | Lau et al. |
| 5,449,379 A | 9/1995 | Hadtke |
| 5,496,262 A | 3/1996 | Johnson, Jr. et al. |
| 5,507,792 A | 4/1996 | Mason |
| 5,509,894 A | 4/1996 | Mason et al. |
| 5,528,485 A | 6/1996 | Devilbiss et al. |
| 5,561,981 A | 10/1996 | Quisenberry et al. |
| 5,566,062 A | 10/1996 | Quisenberry et al. |
| D376,013 S | 11/1996 | Sandman et al. |
| 5,578,022 A | 11/1996 | Scherson et al. |
| 5,588,954 A | 12/1996 | Ribando et al. |
| 5,591,200 A | 1/1997 | Cone et al. |
| 5,648,716 A | 7/1997 | Devilbiss et al. |
| D383,546 S | 9/1997 | Amis et al. |
| D383,547 S | 9/1997 | Mason et al. |
| D383,848 S | 9/1997 | Mason et al. |
| 5,662,695 A | 9/1997 | Mason et al. |
| 5,672,152 A | 9/1997 | Mason et al. |
| 5,675,473 A | 10/1997 | McDunn et al. |
| 5,682,748 A | 11/1997 | DeVilbiss et al. |
| 5,689,957 A | 11/1997 | DeVilbiss et al. |
| 5,690,849 A | 11/1997 | DeVilbiss et al. |
| 5,711,155 A | 1/1998 | DeVilbiss et al. |
| D393,073 S | 3/1998 | Downing et al. |
| 5,731,954 A | 3/1998 | Cheon |
| D394,707 S | 5/1998 | Tsubooka |
| 5,755,755 A | 5/1998 | Panyard |
| 5,772,618 A | 6/1998 | Mason et al. |
| 5,782,780 A | 7/1998 | Mason et al. |
| 5,795,312 A | 8/1998 | Dye |
| 5,807,294 A | 9/1998 | Cawley et al. |
| 5,827,208 A | 10/1998 | Mason |
| 5,831,824 A | 11/1998 | McDunn et al. |
| D403,779 S | 1/1999 | Davis et al. |
| D404,490 S | 1/1999 | Tripolsky |
| D405,884 S | 2/1999 | Roper |
| 5,871,526 A | 2/1999 | Gibbs et al. |
| 5,890,371 A | 4/1999 | Rajasubramanian et al. |
| 5,901,037 A | 5/1999 | Hamilton et al. |
| 5,923,533 A | 7/1999 | Olson |
| 5,980,561 A | 11/1999 | Kolen et al. |
| 5,989,285 A | 11/1999 | DeVilbiss et al. |
| 6,007,559 A | 12/1999 | Arkans |
| 6,055,157 A | 4/2000 | Bartilson |
| 6,058,010 A | 5/2000 | Schmidt et al. |
| 6,058,712 A | 5/2000 | Rajasubramanian et al. |
| 6,080,120 A | 6/2000 | Sandman et al. |
| D428,153 S | 7/2000 | Davis |
| D430,288 S | 8/2000 | Mason et al. |
| D430,289 S | 8/2000 | Mason et al. |
| 6,125,036 A | 9/2000 | Kang et al. |
| 6,129,688 A | 10/2000 | Arkans |
| 6,135,116 A | 10/2000 | Vogel et al. |
| 6,176,869 B1 | 1/2001 | Mason et al. |
| 6,238,427 B1 | 5/2001 | Matta |
| 6,260,890 B1 | 7/2001 | Mason |
| 6,270,481 B1 | 8/2001 | Mason et al. |
| 6,295,819 B1 | 10/2001 | Mathiprakasam et al. |
| 6,305,180 B1 | 10/2001 | Miller et al. |
| 6,319,114 B1 | 11/2001 | Nair et al. |
| 6,352,550 B1 | 3/2002 | Gildersleeve et al. |
| 6,358,219 B1 | 3/2002 | Arkans |
| 6,368,592 B1 | 4/2002 | Colton et al. |
| 6,436,064 B1 | 8/2002 | Kloecker |
| 6,462,949 B1 | 10/2002 | Parish, IV et al. |
| 6,508,831 B1 | 1/2003 | Kushnir |
| D472,322 S | 3/2003 | Hoglund et al. |
| 6,551,264 B1 | 4/2003 | Cawley et al. |
| D474,544 S | 5/2003 | Hoglund et al. |
| 6,562,060 B1 | 5/2003 | Momtaheni |
| 6,596,016 B1 | 7/2003 | Vreman |
| 6,648,904 B2 | 11/2003 | Altshuler et al. |
| D484,601 S | 12/2003 | Griffiths et al. |
| D484,602 S | 12/2003 | Griffiths et al. |
| 6,660,027 B2 | 12/2003 | Gruszecki et al. |
| 6,667,883 B1 | 12/2003 | Solis et al. |
| 6,675,072 B1 | 1/2004 | Kerem |
| D486,870 S | 2/2004 | Mason |
| 6,695,823 B1 | 2/2004 | Lina et al. |
| 6,719,713 B2 | 4/2004 | Mason |
| 6,719,728 B2 | 4/2004 | Mason et al. |
| 6,736,787 B1 | 5/2004 | McEwen et al. |
| D492,411 S | 6/2004 | Bierman |

| | | |
|---|---|---|
| 6,775,137 B2 | 8/2004 | Chu et al. |
| D496,108 S | 9/2004 | Machin et al. |
| 6,789,024 B1 | 9/2004 | Kochan, Jr. et al. |
| 6,802,823 B2 | 10/2004 | Mason |
| D499,846 S | 12/2004 | Cesko |
| 6,834,712 B2 | 12/2004 | Parish et al. |
| 6,846,295 B1 | 1/2005 | Ben-Nun |
| 6,848,498 B2 | 2/2005 | Seki et al. |
| 6,855,158 B2 | 2/2005 | Stolpmann |
| 6,893,414 B2 | 5/2005 | Goble et al. |
| D506,553 S | 6/2005 | Tesluk |
| 6,935,409 B1 | 8/2005 | Parish, IV et al. |
| 6,936,019 B2 | 8/2005 | Mason |
| D510,140 S | 9/2005 | Brown |
| D510,626 S | 10/2005 | Krahner et al. |
| D515,218 S | 2/2006 | McGuire et al. |
| D523,147 S | 6/2006 | Tesluk |
| 7,066,949 B2 | 6/2006 | Gammons et al. |
| 7,081,128 B2 | 7/2006 | Hart et al. |
| D533,668 S | 12/2006 | Brown |
| D551,351 S | 9/2007 | Silva |
| 7,306,568 B2 | 12/2007 | Diana |
| 7,354,411 B2 | 4/2008 | Perry et al. |
| D568,482 S | 5/2008 | Gramza et al. |
| 7,429,252 B2 | 9/2008 | Sarangapani |
| 7,484,552 B2 | 2/2009 | Pfahnl |
| 7,492,252 B2 | 2/2009 | Maruyama |
| D601,707 S | 10/2009 | Chouiller |
| D608,006 S | 1/2010 | Avitable et al. |
| D612,947 S | 3/2010 | Turtzo et al. |
| D618,358 S | 6/2010 | Avitable et al. |
| D619,267 S | 7/2010 | Beckwith et al. |
| D620,122 S | 7/2010 | Cotton |
| D625,018 S | 10/2010 | Smith et al. |
| D626,241 S | 10/2010 | Sagnip et al. |
| D626,242 S | 10/2010 | Sagnip et al. |
| D626,243 S | 10/2010 | Sagnip et al. |
| D626,245 S | 10/2010 | Sagnip et al. |
| D627,896 S | 11/2010 | Matsuo et al. |
| D628,300 S | 11/2010 | Caden |
| D630,759 S | 1/2011 | Matsuo et al. |
| 7,871,387 B2 | 1/2011 | Tordella et al. |
| D634,437 S | 3/2011 | Gramza et al. |
| D634,851 S | 3/2011 | Chiang |
| D635,266 S | 3/2011 | Chiang |
| D635,267 S | 3/2011 | Chiang |
| 7,896,910 B2 | 3/2011 | Schirrmacher et al. |
| D636,497 S | 4/2011 | Giaccone |
| D638,950 S | 5/2011 | Janzon |
| D640,380 S | 6/2011 | Tweardy et al. |
| D640,381 S | 6/2011 | Tweardy et al. |
| 2001/0039439 A1 | 11/2001 | Elkins et al. |
| 2002/0116041 A1 | 8/2002 | Daoud |
| 2003/0089486 A1 | 5/2003 | Parish et al. |
| 2003/0089487 A1 | 5/2003 | Parish, IV et al. |
| 2003/0127215 A1 | 7/2003 | Parish, IV et al. |
| 2003/0135252 A1 | 7/2003 | MacHold et al. |
| 2003/0163183 A1 | 8/2003 | Carson |
| 2004/0008483 A1 | 1/2004 | Cheon |
| 2004/0030281 A1 | 2/2004 | Goble et al. |
| 2004/0046108 A1 | 3/2004 | Spector |
| 2004/0054307 A1 | 3/2004 | Mason et al. |
| 2004/0068309 A1 | 4/2004 | Edelman |
| 2004/0099407 A1 | 5/2004 | Parish, IV et al. |
| 2004/0193218 A1 | 9/2004 | Butler |
| 2004/0221604 A1 | 11/2004 | Ota et al. |
| 2004/0260231 A1 | 12/2004 | Goble et al. |
| 2005/0004636 A1 | 1/2005 | Noda et al. |
| 2005/0006061 A1 | 1/2005 | Quisenberry et al. |
| 2005/0033390 A1 | 2/2005 | McConnell |
| 2005/0039887 A1 | 2/2005 | Parish, IV et al. |
| 2005/0070828 A1 | 3/2005 | Hampson et al. |
| 2005/0070835 A1 | 3/2005 | Joshi |
| 2005/0133214 A1 | 6/2005 | Pfahnl |
| 2005/0143797 A1 | 6/2005 | Parish et al. |
| 2005/0177093 A1 | 8/2005 | Barry et al. |
| 2005/0182364 A1 | 8/2005 | Burchman |
| 2005/0256556 A1 | 11/2005 | Schirrmacher et al. |
| 2005/0274120 A1 | 12/2005 | Quisenberry et al. |
| 2005/0284615 A1 | 12/2005 | Parish et al. |
| 2006/0034053 A1 | 2/2006 | Parish et al. |
| 2006/0058714 A1 | 3/2006 | Rhoades |
| 2006/0241549 A1 | 10/2006 | Sunnen |
| 2006/0282028 A1 | 12/2006 | Howard et al. |
| 2007/0068651 A1 | 3/2007 | Gammons et al. |
| 2007/0112401 A1 | 5/2007 | Balachandran et al. |
| 2007/0118194 A1 | 5/2007 | Mason et al. |
| 2007/0129658 A1 | 6/2007 | Hampson et al. |
| 2007/0260162 A1 | 11/2007 | Meyer et al. |
| 2007/0282249 A1 | 12/2007 | Quisenberry |
| 2008/0058911 A1 | 3/2008 | Parish et al. |
| 2008/0064992 A1 | 3/2008 | Stewart et al. |
| 2008/0071330 A1 | 3/2008 | Quisenberry |
| 2008/0132976 A1 | 6/2008 | Kane et al. |
| 2008/0249559 A1 | 10/2008 | Brown et al. |
| 2009/0069731 A1 | 3/2009 | Parish et al. |
| 2009/0109622 A1 | 4/2009 | Parish et al. |
| 2009/0149821 A1 | 6/2009 | Scherson et al. |
| 2010/0030306 A1 | 2/2010 | Edelman et al. |
| 2010/0081975 A1 | 4/2010 | Avitable et al. |
| 2010/0137764 A1 | 6/2010 | Eddy |
| 2010/0145421 A1 | 6/2010 | Tomlinson et al. |
| 2010/0249679 A1 | 9/2010 | Perry et al. |
| 2011/0009785 A1 | 1/2011 | Meyer et al. |
| 2011/0071447 A1 | 3/2011 | Liu et al. |
| 2011/0082401 A1 | 4/2011 | Iker et al. |
| 2011/0087142 A1 | 4/2011 | Ravikumar et al. |

FOREIGN PATENT DOCUMENTS

| | | |
|---|---|---|
| DE | 35 22 127 | 1/1987 |
| EP | 0 489 326 | 6/1992 |
| GB | 2373444 A | 9/2002 |
| SU | 689674 | 10/1979 |
| WO | WO-93/09727 | 5/1993 |
| WO | WO-00/40186 | 7/2000 |
| WO | WO-01/14012 | 3/2001 |

OTHER PUBLICATIONS

U.S. Appl. No. 12/730,060, Parish et al.
U.S. Appl. No. 12/708,422, Balachandran et al.
U.S. Appl. No. 12/871,188, Parish et al.
U.S. Appl. No. 13/107,264, Quisenberry.
U.S. Appl. No. 12/364,434, Quisenberry.
Artikis, T., PCT International Preliminary Report on Patentability as mailed Jul. 29, 2005, (10 pgs.).
Tom Lee, T.Y. et al; "Compact Liquid Cooling System for Small, Moveable Electronic Equipment", IEEE Transactions on Components, Hybrids, and Manufacturing Technology, Oct. 15, 1992, vol. 15, No. 5, pp. 786-793.
Copenheaver, Blaine R., "International Search Report" for PCT/US2007/022148 as mailed Apr. 2, 2008, 2 pages.
Young, Lee W., "International Search Report" for PCT/US07/08807 as mailed Mar. 3, 2008, (3 pages).
Mahmoud Karimi Azar Daryany, et al., "Photoinactivation of *Escherichia coli* and *Saccharomyces cerevisiae* Suspended in Phosphate-Buffered Saline-A Using 266- and 355-nm Pulsed Ultraviolet Light", Curr Microbiol, vol. 56, 2008, pp. 423-428.
J. Li, et al., "Enhanced germicidal effects of pulsed UV-LED irradiation on biofilms", Journal of Applied Microbiology, 2010, pp. 1-8.
Cyro/Temp Therapy Systems; Product News Catalogue; Jobst Institute, Inc., 6 pages (Copyright 1982).
U.S. Appl. No. 29/397,856, Quisenberry.
U.S. Appl. No. 29/400,194, Quisenberry.
U.S. Appl. No. 29/400,202, Quisenberry.
U.S. Appl. No. 29/400,212, Quisenberry.

WOUND CARE METHOD AND SYSTEM WITH ONE OR BOTH OF VACUUM-LIGHT THERAPY AND THERMALLY AUGMENTED OXYGENATION

CROSS-REFERENCE TO RELATED APPLICATIONS

This patent application is a continuation of U.S. patent application Ser. No. 11/975,047, filed on Oct. 17, 2007. U.S. patent application Ser. No. 11/975,047 is a Continuation-in-Part of U.S. patent application Ser. No. 11/801,662, filed on May 9, 2007. U.S. patent application Ser. No. 11/975,047 claims priority from, and incorporates by reference the entire disclosure of, U.S. Provisional Patent Application No. 60/852,803, filed on Oct. 19, 2006. U.S. patent application Ser. No. 11/801,662 claims priority from, and incorporates by reference the entire disclosure of, U.S. Provisional Patent Application Ser. No. 60/798,982, filed on May 9, 2006. This application is related to, and hereby incorporates by reference U.S. Provisional Patent Application Ser. No. 60/488,709 filed on Jul. 18, 2003; U.S. Provisional Patent Application Ser. No. 60/550,658 filed on Mar. 5, 2004; and U.S. patent application Ser. No. 10/894,369, filed on Jul. 19, 2004 entitled "COMPRESSION SEQUENCED THERMAL THERAPY SYSTEM," are incorporated herein by reference. This application is also related to, and hereby incorporates by reference, commonly assigned U.S. Pat. Nos. 5,097,829, 5,989,285, and U.S. patent application Ser. No. 09/328,183, filed on Jun. 8, 1998.

BACKGROUND OF THE INVENTION

1. Technical Field

The present invention relates to a wound care method and system with one or both of vacuum-light therapy and thermally augmented oxygenation, and more particularly, but not by way of limitation, to a programmable wound care control unit configured to generate a negative pressure for wound cleaning with light therapy, and, in one embodiment, oxygenation of a wound area for healing in conjunction with high thermal contrast modalities generated by the control unit.

2. Description of the Related Art

An important aspect of patient treatment is wound care. Medical facilities are constantly in need of advanced technology for the cleaning and treatment of skin wounds. The larger the skin wound, the more serious the issues are of wound closure and infection prevention. The rapidity of the migration over the wound of epithelial and subcutaneous tissue adjacent the wound is thus critical. Devices have been developed and/or technically described which address certain aspects of such wound healing. For example, U.S. Pat. No. 6,695,823 to Lina et al. ("Lina") describes a wound therapy device that facilitates wound closure. A vacuum pump is taught for collecting fluids from the wound. WO 93/09727 discloses a solution for wound drainage by utilizing negative pressure over the wound to promote the above references migration of epithelial and subcutaneous tissue over the wound.

In other embodiments, wound treatment is performed using light therapy. For example, U.S. Pat. No. 7,081,128 to Hart et al. ("Hart") describes a method of treating various medical conditions such as, for example, joint inflammation, edema, etc., utilizing an array of Light Emitting Diodes contained on a flexible substrate that may be wrapped around an anatomical feature of the human body. U.S. Pat. No. 6,596,016 to Vreman et al. ("Vreman") discloses a phototherapy garment for an infant having a flexible backing material, a transparent liner, and a flexible printed circuit sheet containing surface-mounted LEDs. The LEDs preferably emit high-intensity blue light, suitable for the treatment of neonatal hyperbilirubinemia. The device may include a portable power supply.

In other embodiments, wound treatment is performed using oxygen. The use of oxygen for the treatment of skin wounds has been determined to be very beneficial in certain medical instances. The advantages are multitudinous and include rapidity in healing. For this reason, systems have been designed for supplying high concentration of oxygen to wound sites to facilitate the healing process. For example, U.S. Pat. No. 5,578,022 to Scherson et al. ("Scherson") teaches an oxygen producing bandage and method. One of the benefits cited in Scherson is the ability to modulate a supply of concentrated hyperbaric oxygen to skin wounds. Although oxygen is beneficial in direct application of predetermined dosages to skin wounds, too much oxygen can be problematic. Oxygen applied to a wound site can induce the growth of blood vessels for stimulating the growth of new skin. Too much oxygen, however, can lead to toxic effects and the cessation of healing of the wound. It would be an advantage, therefore, to maximize the effectiveness of oxygen applied to a wound area by enhancing the absorption rate of oxygen into the skin and tissue fluids. By enhancing the absorption rate of the oxygen in the wound, less exposure time and concomitantly fewer toxic side effects to the endothelial cells surrounding the wound, such as devasculation, occurs. It would be a further advantage, therefore, to utilize existing medical treatment modalities directed toward other aspects of patient therapy to augment oxygenation for wound care.

It has been accepted for many years by medical care providers that patient thermal therapy can be very advantageous for certain injuries and/or post operative recovery. For this reason, thermal therapy has been advanced and many reliable and efficient systems exist today which provide localized thermal therapy to patients in both pre and post surgical environments.

Addressing first thermal therapy systems, several devices have been engineered to deliver temperature controlled fluids through pads or convective thermal blankets to achieve the above purpose. Typically, these devices have a heating or a cooling element, a source for the fluid, a pump for forcing the fluid through the pad or blanket, and a thermal interface between the patient and the temperature controlled fluid. U.S. Pat. No. 4,884,304 to Elkins ("Elkins") is, for example, directed to a mattress cover device which contains liquid flow channels which provide the selective heating or cooling by conduction.

Devices have also been developed for simply providing heat or cooling to a person in bed. Electric blankets containing electric heating elements have been used, for example, to provide heat to people in bed. Likewise, cooling blankets, such as the blanket disclosed in U.S. Pat. No. 4,660,388 to Greene ("Greene"), have also been proposed. Greene discloses a cooling cover having an inflatable pad with plenum chambers at opposite ends thereof. Cool air is generated in a separate unit and directed to the pad and out to a number of apertures on the underside of the pad and against the body of the person using the cover.

A disposable heating or cooling blanket is disclosed in U.S. Pat. No. 5,125,238 to Ragan et al. ("Ragan"), which has three layers of flexible sheeting. Two of the layers form an air chamber while a third layer includes a comfortable layer for contact with the patient. Conditioned air is directed toward the covered person through a multiplicity of orifices in the bottom layers of the blanket.

A temperature controlled blanket and bedding assembly is also disclosed in U.S. Pat. No. 5,989,285 to DeVilbiss et al. ("DeVilbiss"), assigned to the assignee of the present invention. DeVilbiss discloses a temperature controlled blanket and temperature control bedding system having the provision of both recirculating temperature controlled fluid and temperature controlled gas to enhance performance for convectively heating or cooling a patient. Counter-flow or co-flow heat exchanging principles between the temperature controlled liquid and the temperature controlled gas achieve temperature uniformity across different sections of the blanket and the bedding system. Drapes and the temperature controlled bedding system provide a temperature controlled envelope around a person using the bedding system. In one embodiment of the bedding system, the air portion of the bedding system is provided for use with a patient that supplies the fluid portion of the overall bedding system. In another embodiment of the bedding system, the fluid portion of the bedding system is provided for use with a patient bed which supplies the air portion of the overall bedding system.

U.S. Pat. No. 5,097,829 to Quisenberry ("Quisenberry") describes an improved temperature controlled fluid circulating system for automatically cooling a temperature controlled fluid in a thermal blanket with a thermoelectric cooling device having a cold side and a hot side when powered by electricity. The temperature controlled fluid is cooled by the cold side of the cooling device and pumped through, to, and from the blanket through first and second conduits.

Finally, co-pending U.S. patent application Ser. No. 10/894,369, assigned to the assignee of the present invention, teaches a sequential compression blanket for use with heating or cooling therapy. In this particular embodiment, the utilization of thermal therapy with sequential compression in a programmable format which further has the option of the introduction of oxygenation through a perforated membrane disposed between the patient and the thermal therapy pad is taught. These advances in the medical industry have been recognized as advantageous to both the medical care providers as well as the patients. The precise manner of oxygenation application is, however, still in the process of development.

The present invention provides improvements in wound care by providing multiple wound healing approaches such as, for example, the application of negative pressure over the wound area along with light therapy of the wound area, and oxygenation of the wound area in conjunction with thermal therapy. By combining an oxygenation modality that is utilized in conjunction with light and thermal therapy and/or sequential compression in association therewith, the individual benefits of negative wound pressure, light therapy, and oxygenation treatments can be synergistically enhanced.

BRIEF SUMMARY OF THE INVENTION

The present invention relates to a wound care method and system with one or both of vacuum-light therapy and thermally augmented oxygenation. More particularly, one embodiment of the present invention includes a control unit for generating a negative pressure for wound cleaning with light therapy. The control unit may also be configured to deliver oxygen to a wound area in conjunction with high thermal contrast modalities.

According to an embodiment, a system for treatment of a wound area of a patient includes a first treatment pad comprising a plurality of Light Emitting Diodes (LEDs) for cleaning and exposing a wound area to ultraviolet light, a second treatment pad comprising removal ports for exposing the wound area to a negative pressure, and a control unit interoperably connected to the first and second treatment pads for providing a negative pressure and the ultraviolet light to the wound area.

According to another aspect of one embodiment of the invention, a method of treating a wound area of a patient includes cleaning, via a first treatment pad, the wound area, exposing the wound area to ultraviolet light from a plurality of Light Emitting Diodes (LEDs), the plurality of LEDs located on an underside of the first treatment pad, oxygenating, via a second treatment pad, the wound area, and controlling, via a control unit, an intensity of the ultraviolet light emitted from the plurality of LEDs and a rate of oxygenating the wound area.

In another aspect of one embodiment of the invention a system for treatment of a wound area of a patient includes an oxygen supply, a thermal fluid supply, a first treatment pad comprising a plurality of Light Emitting Diodes (LEDs) for cleaning and exposing the wound area to ultraviolet light, a second treatment pad, and a control unit interoperably connected to the first and second treatment pads for providing the oxygenation therapy and the ultraviolet light to the wound area.

In yet another aspect, a treatment pad for a wound area of a patient includes a plurality of Light Emitting Diodes (LEDs) located on an underside of the pad for exposing the wound area to ultraviolet light, a plurality of removal ports for removing undesirable fluid from the wound area, and wherein the ultraviolet light emitted from the plurality of LEDs is adapted to penetrate through several layers of skin to destroy infectious bacteria from the wound area.

In another aspect of one embodiment of the invention, a control unit delivers gas for oxygenation of the wound site along with temperature controlled fluid for thermal therapy. A compression therapy blanket may be used therewith and includes a plurality of gas chambers for receiving gas, such as air, to cause compression, a valve assembly internal to the compression therapy blanket for delivering gas to each of a plurality of air chambers in a predetermined pattern, an inlet port for delivering air from a control unit to the valve assemblies, a plurality of connections for delivering gas from the valve assembly to the plurality of gas/air chambers as well as oxygenation gas, and a wound area lighting system. The plurality of gas/air chambers may comprise four to seven chambers and an electrical signal connection may be provided for transmitting data related to the predetermined pattern to the valve assembly. One embodiment includes the predetermined pattern comprising sequential inflation of the plurality of chambers to produce a series of compression movements peripherally toward a given area of a patient, while another embodiment includes inflating two of the plurality of gas/air chambers simultaneously. The oxygenation is provided via a separate oxygenation gas line which is adapted for filling a localized area on a patient's skin in conjunction with the above referenced hot and cold therapy.

In yet another aspect, the above described compression therapy blanket further comprises a heat transfer fluid bladder for providing the above described temperature therapy in conjunction with oxygenation. The bladder includes a fluid inlet port for delivering heat transfer fluid from the control unit to the heat transfer fluid bladder and a fluid outlet port for delivering heat transfer fluid from the heat transfer fluid bladder to the control unit. The heat transfer fluid bladder delivers thermal treatment to a patient in the form of heat or cold.

Yet a further aspect includes an embodiment of the invention comprising a system for passing heat transfer fluid between a control unit and a blanket in conjunction with oxygenation therapy. The system comprises a reservoir for housing heat transfer fluid for utilization by the system, a flow network in flow communication with the reservoir, and including a junction having at least three branches, wherein a first branch receives heat transfer fluid from the reservoir, a second branch receives the heat transfer fluid returning from the blanket, and a third branch for delivering the heat transfer fluid to the blanket, and a pump for creating a low pressure site at the third branch, wherein the low pressure site causes the heat transfer fluid from the second branch to be pulled into the third branch. In one embodiment of the invention, the three-point junction is generally configured as an inverted Y from a fluid flow standpoint. In this particular embodiment, the oxygenation gas would be delivered in a separate line.

In yet another aspect, one embodiment of the invention includes a system having a control unit for wound cleaning and drainage by negative pressure and light therapy together. The control unit may also be adapted for this wound care alone or in one embodiment, the subsequent delivery of thermal fluid with oxygenation as described above. For said oxygenation step, the system may include a thermal therapy blanket with at least one spacing member facilitating a separation of a lower surface of the blanket relative to a skin area of the patient for facilitating the receipt of oxygenation gas therein for the treatment of a wound area therebeneath, which wound area is also thermally exposed to the blanket for first heating and opening pores of the skin to expose capillaries to facilitate the saturation of the skin area with oxygen prior to the cooling thereof which helps close the area and pull oxygen into the underlying tissue.

In another embodiment, the above-described oxygenation method includes the steps of continuing oxygenation at the wound site at one to two atmospheres while lowering the treatment pad fluid to thirty degrees to forty degrees below body temperature to help close the wound area and pull oxygen into the tissues for a period of time on the order between thirty to forth-five minutes. In another embodiment, the process is repeated periodically with the wound being first cleaned of dead tissue by negative pressure, in a first treatment modality utilizing light therapy and then in a second treatment modality, a thermal blanket of the type described above is next utilized over the wound site for said oxygenation and thermal therapy. In one embodiment, a single control unit may control and effectuate both treatment modalities.

BRIEF DESCRIPTION OF THE DRAWINGS

A more complete understanding of the method and apparatus of the present invention may be obtained by reference to the following Detailed Description when taken in conjunction with the accompanying Drawings wherein.

DETAILED DESCRIPTION OF THE INVENTION

Various embodiments of the present invention will now be described more fully with reference to the accompanying drawings. The invention may, however, be embodied in many different forms and should not be construed as limited to the embodiments set forth herein; rather, the embodiments are provided so that this disclosure will be thorough and complete, and will fully convey the scope of the invention to those skilled in the art.

Figure 1:
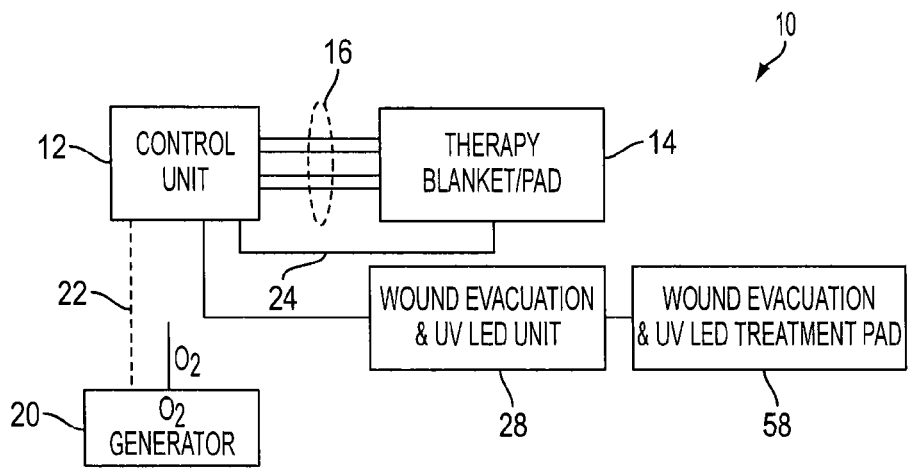
FIG. 1 is an illustration of the wound care system according to an embodiment of the present invention.

Referring first to FIG. 1, there is shown an illustration of one embodiment of a wound care system 10 in accordance with principles of the present invention. The system 10 comprises a control unit 12, a therapy blanket/pad 14 and a plurality of tubular members 16 (to be defined below) connecting the control unit 12 to the therapy blanket/pad 14. The system 10 further includes a wound evacuation and ultra violet light emitting diode (UV LED) unit 28 and a wound evacuation and UV LED treatment pad 58. The wound evacuation and UV LED unit 28 is connected to the control unit 12 while the wound evacuation and UV LED treatment pad 58 is connected to the wound evacuation and UV LED unit 28. A system for providing both oxygenation therapy in conjunction with certain aspects of thermal therapy and fully describing the thermal operation and sequence compression aspects of one embodiment of the present invention is set forth and shown in U.S. patent application Ser. No. 10/894,369, assigned to the assignee of the present invention and incorporated herein in its entirety by reference. For that reason, thermal detail relative to the interaction between the control unit 12 and the therapy blanket/pad 14 relative to the thermal fluid flow and pressurization for sequenced compression therapy is not further defined herein. What is defined, is the added aspect of wound care provided by wound evacuation and light therapy. Light therapy is the application of light energy to the skin for therapeutic benefits. LED light therapy promotes wound healing and human tissue growth. Energy delivered by the LEDs enhances cellular metabolism, accelerates the repair and replenishment of damaged skin cells, as well as stimulates the production of collagen which is the foundation of a healthy and smooth skin. Light therapy is non-ablative, non-invasive, and painless.

Still referring to FIG. 1, the use of the therapy blanket/pad 14 to the wound site of the patient may be, in one embodiment, subsequent to the cleaning of the wound area of dead tissue by the wound evacuation and UV LED treatment pad 58. In one embodiment, Velcro cross straps may be utilized to secure the therapy blanket/pad 14. A 93% concentration of oxygen has been suggested to be advantageous when applied to a wound site as described herein with one or two atmospheres of pressure. In accordance with one aspect of the present invention, an oxygen generator/concentrator 20 may be utilized within the control unit 12 or may be separate therefrom. In FIG. 1, an oxygen generator/concentrator 20 is shown in association with the control unit 12 by dotted line 22 and an oxygenation gas line 24 shown extending between the control unit 12 and the therapy blanket/pad 14 as a diagrammatic illustration according to an embodiment of the present invention.

In FIG. 1, fiber optic strands (not explicitly shown) direct ultraviolet light from a plurality of LEDs (not explicitly shown) to an array of fiber optic strand ends (not explicitly shown) located on the undersurface of wound evacuation and UV LED treatment pad 58. The control unit 12 may be used to modulate the ultraviolet light to create various patterns of light, different intensities of light, and different durations of light. The ultraviolet light is capable of penetrating through several layers of skin to destroy infectious bacteria. In one embodiment, not specifically shown herein, the UV LED treatment pad 58 may be provided on the therapy blanket/pad 14. According to exemplary embodiments, the ultraviolet light from the plurality of LEDs located on the undersurface of wound evacuation and UV LED treatment pad 58 destroys a wide variety of microorganisms such as, for example, bacteria which causes skin infections. In addition, the ultraviolet light from the plurality of LEDs improves wound healing along with cell and bone growth. Furthermore, the use of LEDs in light therapy is safe, non-invasive, drug-free and therapeutic.

Figure 2:
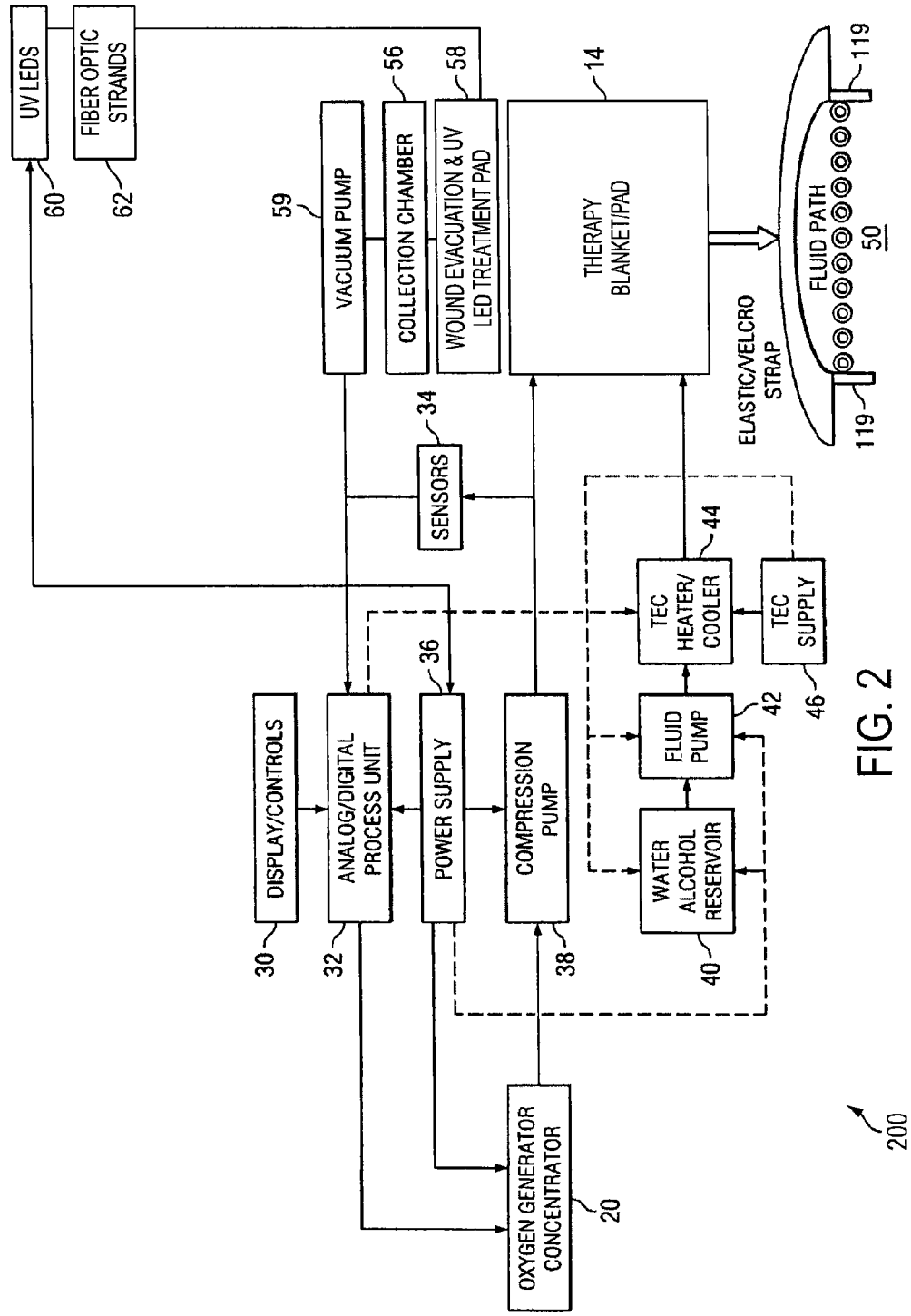
FIG. 2 is a block diagram according to an embodiment of the present invention.

Referring now to FIG. 2, there is a block diagram 200 illustrating the flow of oxygenation gas as a transfer fluid according to an embodiment of the present invention. As set forth in the block diagram 200, a control unit display 30 is provided in conjunction with an analog/digital processing unit 32. The process is referred to herein as "oxytherm" which is the term currently being utilized by the Applicant of the present invention through its assignee in preparation for commercial disclosure of certain ones of the methods, systems and principles of the present invention.

Still referring to FIG. 2, a plurality of sensors 34 are utilized in conjunction with the processing unit 32 for control of heat transfer fluids to the therapy blanket/pad 14 as well as the oxygen delivery thereto. The oxygen generator/concentrator 20 is connected to a power supply 36, which power supply 36, also powers the processing unit 32. The oxygen generated from the oxygen generator/concentrator 20 is then pumped through compression pump 38 before delivery to the therapy blanket/pad 14. It should be noted that an oxygen supply may also be used.

Referring still to FIG. 2, a water/alcohol reservoir 40 is shown in fluid flow communication with fluid pump 42 and Thermo Electric Cooler (TEC) heater/cooler 44. The TEC heater/cooler 44 is controlled by the processing unit 32 and a TEC supply 46 is likewise shown. Adjacent the TEC supply 46 is illustrated a diagrammatical schematic of a treatment chamber 50 defined beneath the therapy blanket/pad 14 wherein the treatment chamber 50 is thermally exposed to the thermal fluid by the fluid path therein illustrated. The adhesive attachment edges 52 therein shown likewise define the treatment chamber space 50 between the therapy blanket/pad 14 and the wound site to allow for the flow of the oxygenation gas therein.

Referring still to FIG. 2, there is shown a vacuum pump 59 powered by the power supply 36. A collection chamber 56 is connected to the vacuum pump 54 and to a wound evacuation and UV LED treatment pad 58. The wound evacuation and UV LED treatment pad 58 is used prior to the therapy blanket/pad 14, in one embodiment of the present invention, for cleaning the wound area in preparation for oxygenation in conjunction with thermal therapy in accordance with the present invention.

Referring still to FIG. 2, there is shown a plurality of ultraviolet LEDs 60 and fiber optic strands 62, which are interoperably connected to the wound evacuation and UV LED treatment pad 58. The wound evacuation and UV LED treatment pad 58 is used prior to the therapy blanket/pad 14, in one embodiment of the present invention, for removing bacteria from the wound area in preparation for oxygenation in conjunction with thermal therapy in accordance with the present invention. According to exemplary embodiments, the ultraviolet light from the plurality of LEDs located on the undersurface of wound evacuation and UV LED treatment pad 58 destroys a wide variety of microorganisms such as, for example, bacteria which causes skin infections. In addition, the ultraviolet light from the plurality of LEDs improves wound healing along with cell and bone growth. Furthermore, the use of LEDs in light therapy is safe, non-invasive, drug-free and therapeutic.

According to exemplary embodiments, the ultraviolet light from the plurality of LEDs located on the undersurface of wound evacuation and UV LED treatment pad 58 is in the range of approximately 200 to 450 nanometers and higher, and energy levels of up to 35,000 microwatt seconds/cm$^2$, which are necessary to eliminate or destroy most microorganisms such as bacteria, spores, algae and viruses. Most bacteria can be destroyed at ultra violet energies of from about 3,000 to about 5,000 microwatt-seconds/cm$^2$ while mold spores may require energies in the 20,000 to 35,000 mW-seconds/cm$^2$.

Figure 3:
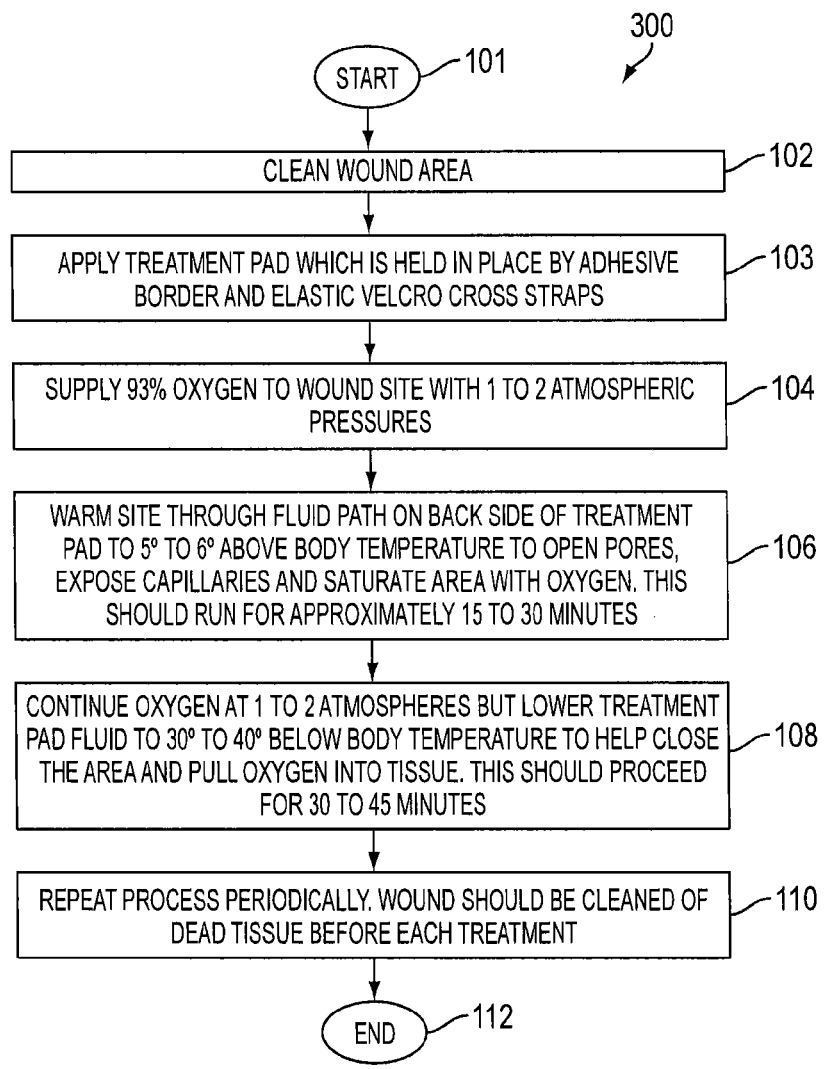
FIG. 3 is a flow diagram of a process according to an embodiment of the present invention.

Referring now to FIG. 3 there is shown a flow diagram of a process 300 according to an embodiment of the present invention. The process 300 starts at step 101. At step 102, the wound area is cleaned of dead tissue, any undesirable fluids, and bacteria by applying the wound evacuation and UV LED treatment pad 58. The wound evacuation and UV LED treatment pad 58 is used prior to the therapy blanket/pad 14 for removing bacteria from the wound area in preparation for oxygenation in conjunction with thermal therapy in accordance with the present invention. According to exemplary embodiments, the ultraviolet light from the plurality of LEDs located on the undersurface of wound evacuation and UV LED treatment pad 58 destroys a wide variety of microorganisms such as, for example, bacteria which causes skin infections. In addition, the ultraviolet light from the plurality of LEDs improves wound healing along with cell and bone growth. Furthermore, the use of LEDs in light therapy is safe, non-invasive, drug-free and therapeutic.

At step 103, the therapy blanket/pad 14 is applied to the wound area. The therapy blanket/pad 14 is held in position by an adhesive border and, in one embodiment, elastic Velcro cross straps. At step 104, according to an embodiment, an oxygenation gas comprising on the order of 93% concentration of oxygen gas is delivered to the wound site with one to two atmospheric pressures. The numbers as set forth and shown are exemplary and other oxygenation concentrations as well as pressures are contemplated in accordance with the principles of the present invention. Consistent therewith, however, is the concept of, and teachings for, thermal treatment of the wound site in conjunction with the oxygenation. In accordance therewith, the site is thus warmed through the fluid path herein shown on the back side of the therapy blanket/pad 14 up to 5 to 6 degrees above the body temperature of the patient in step 106. This warming allows the pore of the patient's skin to open and expose capillaries therein. The capillaries of the skin are then saturated with oxygen. In one period of time herein described, a period of 15 to 30 minutes is recommended. At step 108, oxygenation is continued at one to two atmospheres and the therapy blanket/pad fluid is lowered to 30 to 40 degrees below body temperatures to help close the pores of the area and pull oxygen into the underlying tissue. This step then proceeds for approximately for 30 to 45 minutes in accordance with an embodiment of the present invention. At step 110, the process 300 may be repeated periodically and the wound site may be cleaned of dead tissue before each treatment. At step 112, the process 300 ends.

Figure 4:
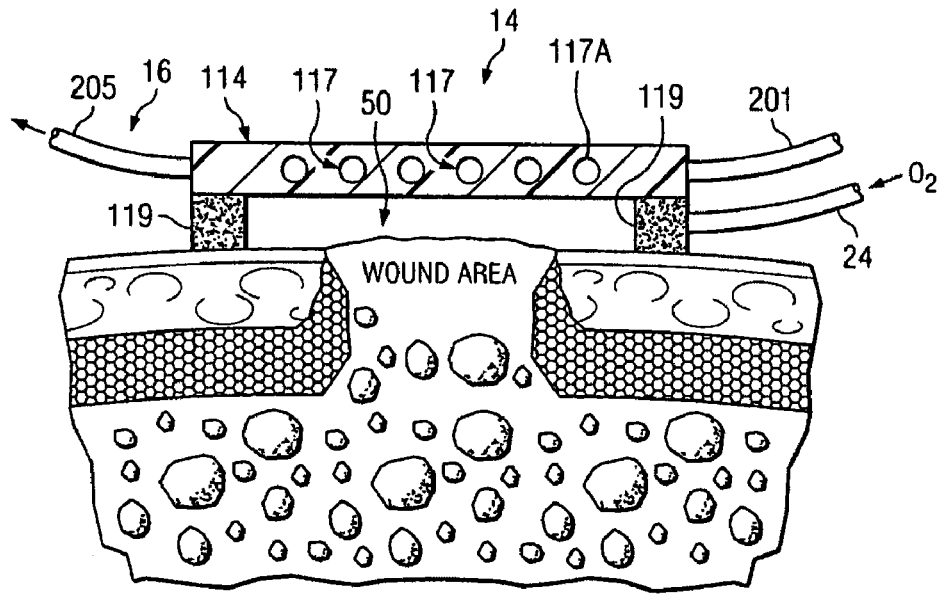
FIG. 4 illustrates a side elevational cross sectional view of a therapy blanket/pad according to an embodiment of the present invention.

FIG. 4 is a side elevational, cross sectional view of one embodiment of the therapy blanket/pad 14 of the present invention. In this embodiment, the therapy blanket/pad 14 is constructed within a single bladder configuration 114 where thermal fluid flow may be provided. The tubes 16 are coupled to the therapy blanket/pad 14, which is fabricated with a circuitous flow path therein for thermal fluid flow. This path may be tubular in form, or simply a path within therapy blanket/pad 14 defined by flow channels. What is shown is a path 117 within therapy blanket/pad 14. The path 117 is shown with tubular ends 117A, for example, in order to illustrate that thermal fluid flows therein for thermal treatment of the underlying wound area. Again, the path 117 may not be of tubular form and may have a variety of shapes and fabrication techniques well know in the art of thermal pads.

According to an exemplary embodiment, the therapy blanket/pad 14 is separated from the patient's skin by adhesive strips 119 having a thickness of, for example, ⅛ inch. The therapy blanket/pad 14 (not drawn to scale) exposes the wound to heat and then cold via path 117 while oxygen is injected into chamber 50. The injection of oxygen in conjunction with the aforesaid heating and cooling via path 117 helps treat the wound and any stasis zones therein where tissue swelling has restricted the flow of blood to the wound tissues. It is well known that without sufficient blood flow the epithelial and subcutaneous tissues referenced above receive less oxygen and are less able to migrate over the wound to promote healing. By utilizing the methods and apparatus of the present invention, oxygenation is enhanced and the problems associated with such conditions mitigated.

Figure 5:
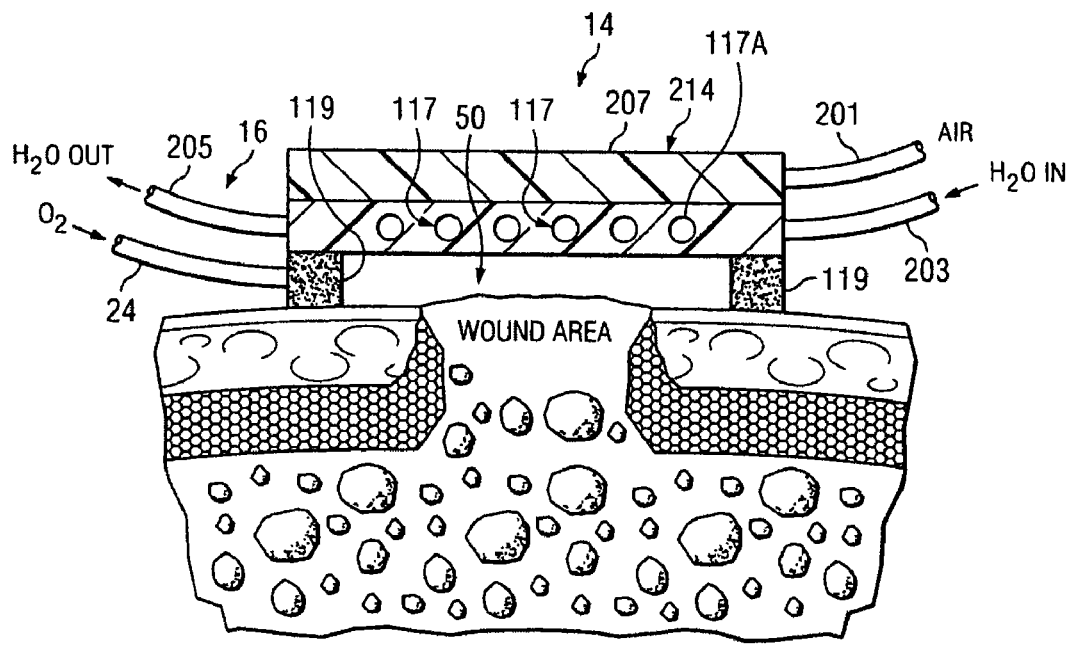
FIG. 5 illustrates a side elevational cross sectional view of a therapy blanket/pad according to an alternate embodiment of the present invention.

FIG. 5 illustrates an alternative embodiment of the thermal therapy and oxygenation treatment pad of FIG. 4. A dual bladder configuration 214 is thus provided where air may be applied to bladder 207 atop the thermal flow tubes 117, also represented by the "tubular" ends 117A shown for purposes of example only. In this manner, select compression therapy may be afforded in conjunction with the thermal and oxygenation treatment. In that regard, air inlet tube 201 is illustrated in connection to bladder 207. Both FIGS. 4 and 5 show oxygen tube 24 for feeding oxygen to chamber 50, with tube 203 allowing thermal fluid into conduits 117 with tube 205 allowing thermal fluid return to control unit 12 of FIG. 1. FIG. 5 further illustrates the advantages of FIG. 4 with the ability for either compression or sequenced compression as referenced above.

Figure 6:
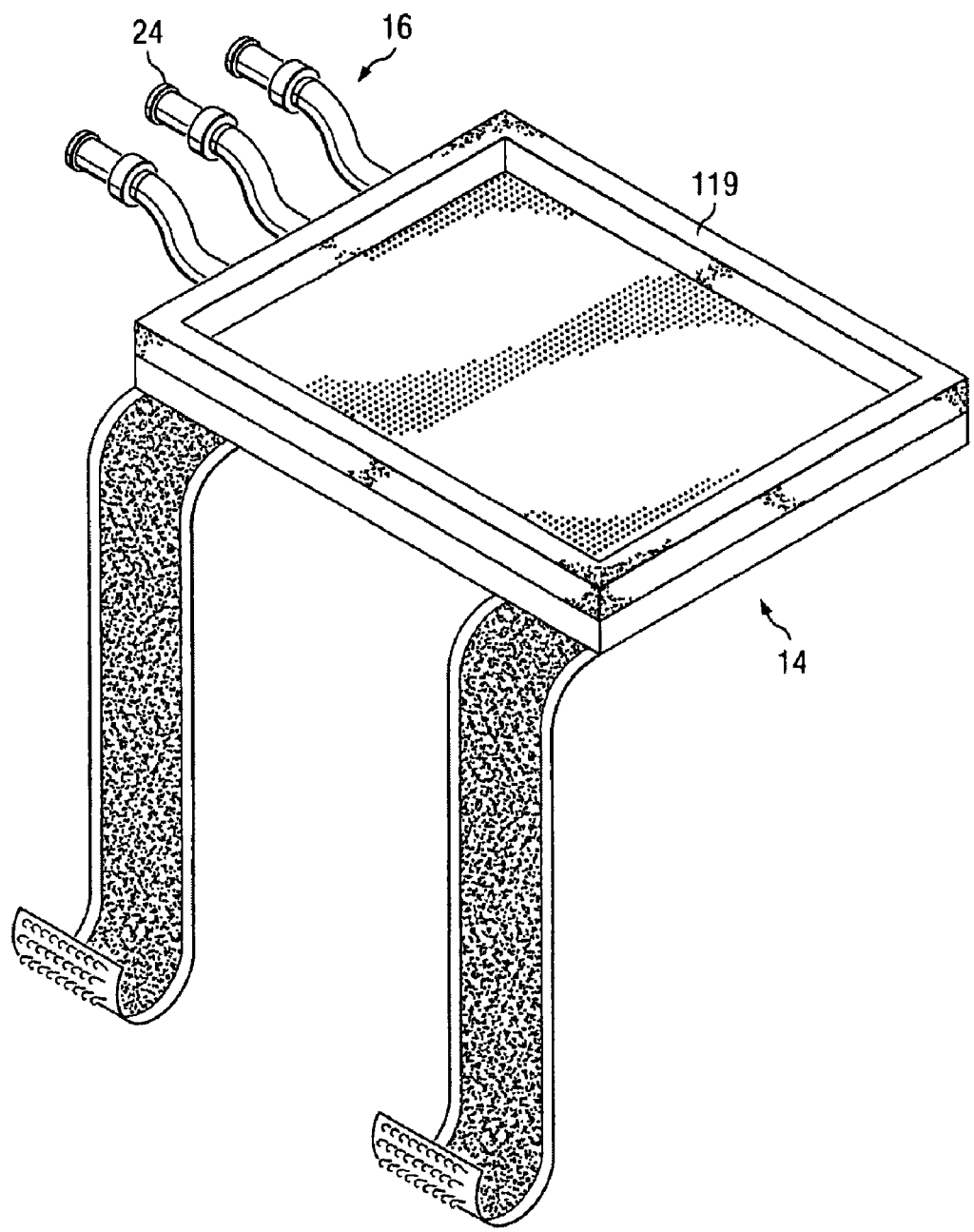
FIG. 6 is a diagrammatic illustration of a therapy blanket/pad according to an embodiment of the present invention.

Referring now to FIG. 6, there is shown a diagrammatic illustration of a therapy blanket/pad 14 of FIGS. 1 and 4. The tubular connections 16 for thermal fluid flow and the tube 24 for oxygen flow is clearly seen. The adhesive border 119 is likewise shown, as further outlined for clarity in the photograph of the prototype shown herein.

Figure 7:
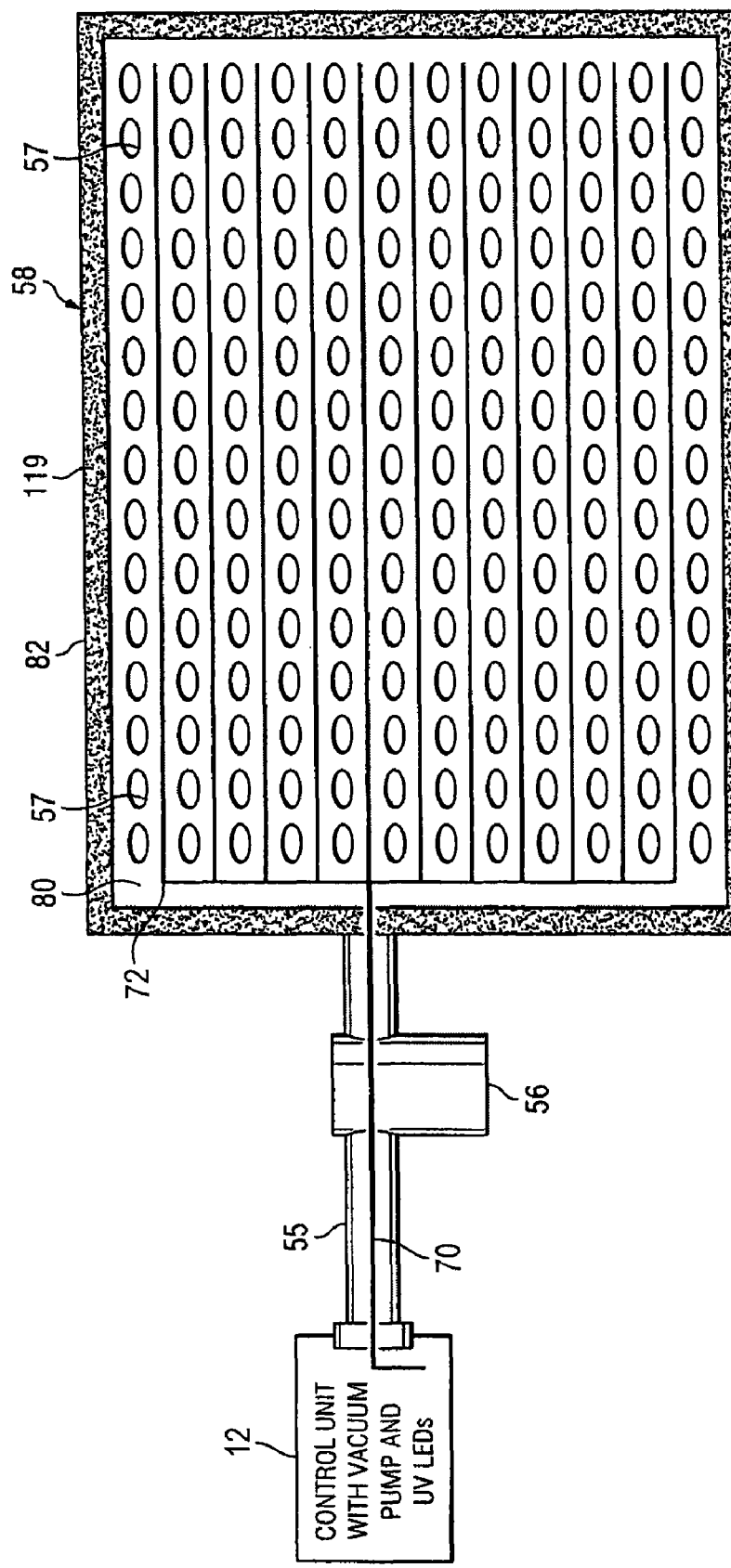
FIG. 7 is a diagrammatic illustration of a wound evacuation and UV LED treatment pad according to an embodiment of the present invention.

FIG. 7 is diagrammatic illustration of a wound evacuation and UV LED treatment pad 58 according to an embodiment of the present invention. In this embodiment, the wound evacuation and UV LED treatment pad 58 contains an array of fiber optic strand ends 72 to project ultraviolet light onto a wound area (not explicitly shown). The wound evacuation and UV LED treatment pad 58 also contains an array of unique removal ports 57 that may be used to remove any undesirable fluid from the wound area. The wound evacuation and UV LED treatment pad 58 further contains a non-tissue adhesive service 80 which contains both the fiber optic strand array 72 and the unique removal ports 57. An adhesive circumference 82 is located around the periphery of the wound evacuation and UV LED treatment pad 58 to allow for a seal to be formed around the wound area. The seal, in conjunction with the removal ports 57, allows for a negative pressure to form over the wound area, which facilitates the removal the undesirable tissues from the wound area. The device also includes a control unit 12, which contains a vacuum pump (not shown) and a plurality of ultraviolet LEDs (not explicitly shown). The vacuum pump is connected to the wound evacuation and UV LED treatment pad 58 via a vacuum line 55. A collection chamber 56 is positioned inline between the vacuum pump and the wound evacuation and UV LED treatment pad 58 to intercept and store any undesirable fluids or the like that are removed from the wound area as a result of applying a negative pressure to the wound area with the vacuum pump. The plurality of ultraviolet LEDs transmit ultraviolet light through fiber optic strands 70 to the wound evacuation and UV LED treatment pad 58, where the strands are then dispersed throughout the wound evacuation and UV LED treatment pad 58 to project ultraviolet light onto the wound area. Energy delivered by the plurality of LEDs enhances cellular metabolism, accelerates the repair and replenishment of damaged skin cells, as well as stimulates the production of collagen which is the foundation of a healthy and smooth skin. Light therapy is non-ablative, non-invasive, and painless.

The previous Detailed Description is of embodiment(s) of the invention. The scope of the invention should not necessarily be limited by this Description. The scope of the invention is instead defined by the following claims and the equivalents thereof.

What is claimed is:
1. A method of treating a wound area of a patient, comprising:
providing a first pad comprising:
a plurality of fiber-optic strands coupled to a plurality of light-emitting diodes, the plurality of fiber-optic strands comprising a plurality of fiber-optic strand ends arranged in an array on an underside of the first pad; and
a plurality of removal ports in fluid communication with a collection chamber, a vacuum pump, and at least one first tube;
providing a second pad comprising:
a bladder in fluid communication with at least one of a heat-transfer fluid reservoir and a thermoelectric element via a fluid pump and a plurality of second tubes, the bladder and the plurality of second tubes defining a circuitous first flow path for a heat-transfer fluid; and
a plurality of tubular connections in fluid communication with an oxygen source thereby defining a second flow path that provides oxygen to the wound area;
wherein the first pad and the second pad are coupled to a processing unit, the processing unit capable of controlling the light-emitting diodes, the vacuum pump, the thermoelectric element, and the fluid pump as follows:
exposing the wound area to ultraviolet light via the plurality of fiber-optic strand ends thereby cleaning the wound area;
exposing the wound area to negative pressure via the plurality of removal ports thereby cleaning the wound area;
circulating the heat-transfer fluid through the circuitous first flow path after said exposing the wound area to ultraviolet light and said exposing the wound area to negative pressure;
increasing a temperature of the wound area above a body temperature of the patient via the heat transfer fluid;
oxygenating the wound area via the plurality of tubular connections within the second pad after said increasing the temperature of the wound area; and simultaneous to said oxygenating, decreasing the temperature of the wound area below the body temperature of the patient via the heat transfer fluid.

2. The method of claim 1 further comprising:
controlling, via the processing unit, a duration of the ultraviolet light emitted from the plurality of light-emitting diodes.

3. The method of claim 1, further comprising providing, via an air bladder disposed in the second pad, compression therapy to the wound area.

4. The method of claim 1, further comprising securing the second pad to the wound area via an adhesive border disposed around a perimeter of the second pad.

5. The method of claim 1, wherein said oxygenating comprises supplying oxygen-rich air to the wound area.

6. The method of claim 5, further comprising generating the oxygen-rich air via an oxygen concentrator.

7. The method of claim 5, wherein the oxygen-rich air comprises approximately 93% oxygen.

8. The method of claim 1, wherein said oxygenating occurs at a pressure of approximately 1 to approximately 2 atmospheres.

9. The method of claim 1, wherein said warming comprises warming the heat-transfer fluid to a temperature approximately 5 to approximately 6 degrees above the body temperature.

10. The method of claim 1, wherein said increasing the temperature of the wound area occurs for approximately 15 to approximately 30 minutes.

11. The method of claim 1, wherein said decreasing the temperature of the wound area comprises cooling the heat-transfer fluid to a temperature approximately 30 to approximately 40 degrees below the body temperature.

12. The method of claim 1, wherein said decreasing the temperature of the wound area occurs for approximately 30 to approximately 45 minutes.

13. The method of claim 1, wherein said exposing the wound area to negative pressure removes dead tissue from the wound area.

14. The method of claim 1, wherein said exposing the wound area to ultraviolet light destroys infectious bacteria within the wound area.

15. A method of treating a wound area of a patient, comprising:
providing a first pad comprising a plurality of fiber-optic strands and a plurality of removal ports;
coupling the first pad to a processing unit capable of controlling a vacuum pump fluidly coupled to the plurality of removal ports, a plurality of light-emitting diodes coupled to the plurality of fiber-optic strands, a thermoelectric element, and a compression pump;
exposing the wound area to ultraviolet light via the plurality of fiber-optic strands thereby cleaning the wound area;
exposing the wound area to negative pressure via the plurality of removal ports thereby cleaning the wound area;
coupling a second pad to the processing unit capable of controlling the vacuum pump, the plurality of light-emitting diodes, the thermoelectric element, and the compression pump;
providing at least one of thermal therapy and oxygenation to a wound area via the second pad;
increasing a temperature of the wound area above a body temperature of the patient via the second pad;
oxygenating the wound area via the second pad, wherein said oxygenating occurring after said increasing;
decreasing the temperature of the wound area below the body temperature of the patient via the second pad; and
wherein said oxygenating overlaps in time, at least in part, with said decreasing.

* * * * *

UNITED STATES PATENT AND TRADEMARK OFFICE
CERTIFICATE OF CORRECTION

| | | |
|---|---|---|
| PATENT NO. | : 8,142,486 B2 | Page 1 of 1 |
| APPLICATION NO. | : 13/190564 | |
| DATED | : March 27, 2012 | |
| INVENTOR(S) | : Tony Quisenberry | |

It is certified that error appears in the above-identified patent and that said Letters Patent is hereby corrected as shown below:

Title Page

Replace "(75) Inventors: Tony Quisenberry, Highland Village, TX (US); Niran Balachandran, Lewisville, TX (US)"

With --(75) Inventors: Tony Quisenberry, Highland Village, TX (US)--

Signed and Sealed this
Seventeenth Day of March, 2015

Michelle K. Lee
*Director of the United States Patent and Trademark Office*